United States Patent
Green (10) Patent No.: US 7,435,251 B2
(45) Date of Patent: Oct. 14, 2008

(54) SYSTEM FOR SECURING A SUTURE

(76) Inventor: David T. Green, 40 Madison Hill, Fairfield, CT (US) 06430

( * ) Notice: Subject to any disclaimer, the term of this patent is extended or adjusted under 35 U.S.C. 154(b) by 296 days.

(21) Appl. No.: 10/930,161

(22) Filed: Aug. 31, 2004

(65) Prior Publication Data

US 2006/0047314 A1    Mar. 2, 2006

(51) Int. Cl.
*A61B 17/04* (2006.01)
(52) U.S. Cl. .................. 606/232; 606/142; 606/157
(58) Field of Classification Search .............. 606/144, 606/232, 142, 148, 157; 132/281, 282
See application file for complete search history.

(56) References Cited

U.S. PATENT DOCUMENTS

| | | | |
|---|---|---|---|
| 5,242,456 A * | 9/1993 | Nash et al. ............... | 606/142 |
| 5,258,015 A | 11/1993 | Li et al. | |
| 5,269,783 A | 12/1993 | Sander | |
| 5,403,346 A | 4/1995 | Loeser | |
| 5,425,747 A | 6/1995 | Brotz | |
| 5,462,558 A * | 10/1995 | Kolesa et al. ............. | 606/139 |
| 5,474,567 A * | 12/1995 | Stefanchik et al. ........ | 606/143 |
| 5,520,702 A | 5/1996 | Sauer et al. | |
| 5,531,763 A | 7/1996 | Mastri et al. | |
| 5,669,917 A * | 9/1997 | Sauer et al. ............... | 606/139 |
| 5,827,306 A | 10/1998 | Yoon | |
| 5,931,855 A | 8/1999 | Buncke | |
| 6,010,525 A | 1/2000 | Bonutti et al. | |
| 6,077,277 A | 6/2000 | Mollenauer et al. | |
| 6,086,608 A | 7/2000 | Ek et al. | |
| 6,099,553 A | 8/2000 | Hart et al. | |
| 6,126,677 A | 10/2000 | Ganaja et al. | |
| 6,454,777 B1 | 9/2002 | Green | |
| 2004/0236372 A1 | 11/2004 | Anspach et al. | |

FOREIGN PATENT DOCUMENTS

WO    WO 2004/024006 A    3/2004

OTHER PUBLICATIONS

International Search Report and Written Opinion dated Dec. 12, 2005 in PCT/GB2005/003359.

* cited by examiner

*Primary Examiner*—Todd E Manahan
*Assistant Examiner*—Ryan Severson
(74) *Attorney, Agent, or Firm*—Edwards Angell Palmer & Dodge LLP; Scott D. Wofsy, Esq.

(57) ABSTRACT

A system is disclosed for securing a suture. The system includes a deformable suture clip having a pair of closely spaced panels configured for movement between an open position wherein a suture can pass between the two panels and a closed position wherein the suture can be securely clamped between the two panels. The system further includes a clip applicator having an elongated body defining opposed proximal and distal end portions. The distal end portion of the body includes a mounting fixture having structure for supporting the suture clip in an open position. The clip applicator further includes a mechanism for dislodging the suture clip from the mounting fixture, such that the panels of the clip move to the closed position to securely clamp the suture therebetween.

21 Claims, 5 Drawing Sheets

SYSTEM FOR SECURING A SUTURE

BACKGROUND OF THE INVENTION

1. Field of the Invention

The subject disclosure relates to a system for securing a suture, and more particularly, to a surgical apparatus for applying a deformable suture clip to a suture used to close a surgical incision or wound formed in a blood vessel or body tissue.

2. Background of the Related Art

Sutures have long been used to close wounds and surgical incisions in body tissue. It is common practice to secure a suture in body tissue by tying one or more knots therein. Knots are time consuming to tie, difficult to form in small body cavities and are a relatively unreliable means of securely maintaining a suture in tissue. In view of these shortcomings, various devices and fasteners have been developed to positively secure a suture in place following a surgical procedure.

For example, U.S. Pat. No. 6,077,277 to Mollenauer et al. discloses a device for joining suture segments together. The device has a pair of grasping jaws with heating surfaces thereon configured to weld the suture together. U.S. Pat. No. 6,086,608 to Ek et al. discloses a suture collet that consists of an outer member defining a passage for receiving a suture. An inner member is threaded into the outer member to retain the suture therein. U.S. Pat. No. 5,520,702 to Sauer et al. and U.S. Pat. No. 6,099,553 to Hart et al. each disclose cinches to retain a suture used to close an incision in body tissue.

Certain surgical procedures, such as angioplasty procedures, require the creation of a small percutaneous incision or opening in the femoral artery. Typically, at the conclusion of the procedure, the incision or opening in the blood vessel is closed by applying a fair amount of pressure to the wound until hemostasis occurs. This technique is time consuming, uncomfortable and can cause thrombosis, thereby presenting a danger to the patient. Fortunately, surgical instruments have been developed to mechanically close incisions in blood vessels, thus avoiding the need for the direct application of pressure to close the wound.

A particularly useful device for mechanically closing an incision in the wall of a blood vessel following a surgical procedure is disclosed in U.S. Pat. No. 6,454,777 to Green, which is incorporated herein by reference in its entirety. This device applies a suture to the walls of a blood vessel to close an incision formed therein. Once the suture is placed and the apparatus is withdrawn from the incision site, a knot is formed in the suture to secure it in place. However, because the procedure is performed percutaneously through a small entrance wound in the patient's leg, properly tying a knot to securely fasten the suture and close the incision is a difficult task. For that matter, placing a clip on the suture at the site of the incision in the blood vessel wall is even more difficult, because there is no direct line of sight to ensure the proper placement of the clip.

Clearly, there is a need in the art for an apparatus that is adapted and configured to effectively and accurately apply a clip to a suture used to close an incision formed in the wall of a blood vessel.

SUMMARY OF THE INVENTION

The subject invention is directed to a new and useful system for securing a clip to suture used to close a wound or surgical incision in body tissue, such as an opening in a blood vessel. The system includes a deformable suture clip having a pair of closely spaced panels configured for movement between an open position wherein a suture can pass between the two panels and a closed position wherein the suture can be securely clamped between the two panels. The system further includes a clip applicator having an elongated body defining opposed proximal and distal end portions. The distal end portion of the applicator body includes a mounting fixture or lug having means for releasably supporting the deformable suture clip in an open position. The clip applicator further includes means for dislodging the suture clip from the mounting fixture, such that the panels of the deformable clip move to the closed position to securely clamp the suture therebetween.

Preferably, the clip applicator further includes means for severing or cutting the suture at a location proximal to the suture clip. The severing means is positioned and preferably operates to cut the suture after the suture clip is dislodged from the mounting fixture. The mounting fixture is oriented at an angle with respect to the longitudinal axis of the elongated body of the clip applicator. The helps to properly align and position the clip at the incision site, so that it is flush against the vessel wall or body tissue that has been sutured.

The means for supporting the suture clip in an open position preferably includes a clamp block, which extends distally from the mounting fixture and is dimensioned for insertion between the closely spaced panels of the suture clip. The means for dislodging the suture clip from the mounting fixture preferably includes an elongated translating pusher finger adapted to dislodge the suture clip from the clamp block. The mounting fixture preferably includes an opening, which is dimensioned and configured to provide the pusher finger with access to the suture clip. Preferably, the means for dislodging the clip is manually operable from the proximal end portion of the clip applicator.

The subject invention is also directed to a new and useful deformable suture clip. The suture clip includes a proximal body portion having a pair of abutting surfaces configured for movement between an open position and a normally closed position. In the open position, a suture can pass between the abutting surfaces. In the normally closed position, the suture can be securely clamped between the pair of abutting surfaces. The suture clip further includes a distal body portion defining, at least in part, deformable means for facilitating the movement of the pair of abutting surfaces between the open and closed positions.

The proximal body portion of the suture clip preferably includes a pair of closely spaced panels each forming one of the abutting surfaces. The deformable means preferably includes, at least in part, a deformable panel extending generally parallel to the closely spaced panels of the proximal body portion. It is envisioned that at least the deformable panel of the clip is formed from a metallic material, and preferably from a spring metal or a shape memory alloy. The distal body portion of the clip preferably includes a guide notch or slot for receiving the suture.

The subject invention is also directed to an applicator for applying a deformable clip to a suture used to close an incision or wound in a blood vessel or body tissue. The applicator includes an elongated outer tubular body section defining opposed proximal and distal end portions. The distal end portion of the outer body section is truncated and includes a mounting fixture or lug having means for supporting a deformable suture clip in an open position. The applicator further includes an inner body section cooperatively supported for longitudinal translation within the outer body section. The inner body section includes means for dislodging the suture clip supported on the mounting fixture at the distal end of the outer body section, such that the suture clip moves to a closed position to securely engage the suture at a desired location.

Preferably, the outer body section of the applicator includes a slot for accommodating the passage of the suture from the incision site to a remote location for access by a surgeon. The mounting fixture or lug preferably includes a projection or block for maintaining the clip in an open position. The block fits intimately between the abutting surfaces of the closely spaced panels in the proximal portion of the clip, which are normally biased into a closed position. The mounting fixture also includes means for aligning the suture clip on the distal end of the applicator. The aligning means preferably includes a plurality of stops or tabs, which project from the distal surface of the mounting fixture for contacting the proximal portion of the clip at predetermined locations.

The applicator further comprises means associated with the inner body section for cutting the suture at a location proximal to the clip. Preferably, the means for dislodging the suture clip from the mounting fixture includes an elongated pusher finger that extends distally from the end of the inner body section. Preferably, means are provided for preventing rotation of the inner body section with respect to the outer body section to ensure proper alignment of the pusher finger with the corresponding aperture in the mounting fixture. Means are also provided for limiting axial translation of the inner shell assembly relative to the outer shell assembly. Preferably, the applicator further includes selectively releasable locking means for preventing axial movement of the inner body section relative to the outer body section until such movement is desired.

The subject invention is also directed to a method for applying a clip to a suture at a desired location. The method includes the steps of providing a clip applicator having a deformable clip positioned at a distal end thereof, threading a suture through an opening in the deformable clip, positioning the deformable clip at a desired location on the suture, and dislodging the deformable clip from the distal end of the applicator in such a manner so that the opening through which the suture is threaded is closed to securely clamp the suture. The method further includes the step of cutting the suture at a location proximal to the clip.

These and other unique features of the system, apparatus and method disclosed herein will become more readily apparent from the following description and the accompanying drawings.

BRIEF DESCRIPTION OF THE DRAWINGS

So that those having ordinary skill in the art to which the subject invention appertains will more readily understand how to make and use the same, reference may be had to the drawings wherein.

DETAILED DESCRIPTION OF PREFERRED EMBODIMENTS

Figure 1:
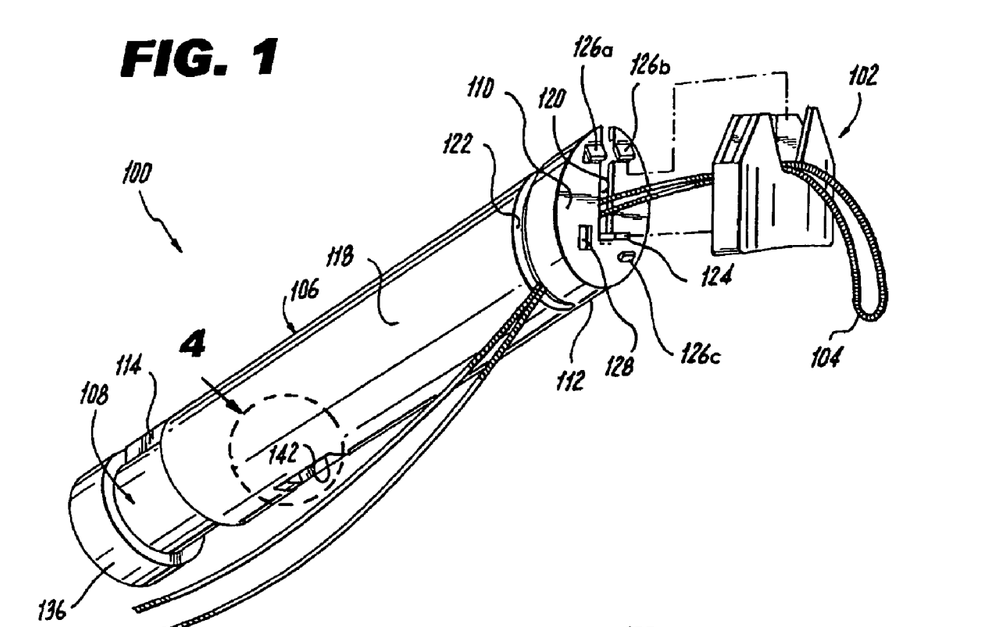
FIG. 1 is a perspective view of a clip applicator constructed in accordance with a preferred embodiment of the subject invention, showing the novel suture clip dislodged from the lug at the distal end of the applicator.

Referring now to the drawings wherein like reference numerals identify similar structural elements of the apparatus disclosed herein, there is illustrated in FIG. 1 a suture clip applicator constructed in accordance with a preferred embodiment of the subject invention and designated generally by reference numeral 100. In the specification that follows the term "distal" shall refer to the end of the applicator that is nearest to the surgical site, while the term "proximal" shall refer to the end of the applicator that is farthest from the surgical site.

Figure 2:
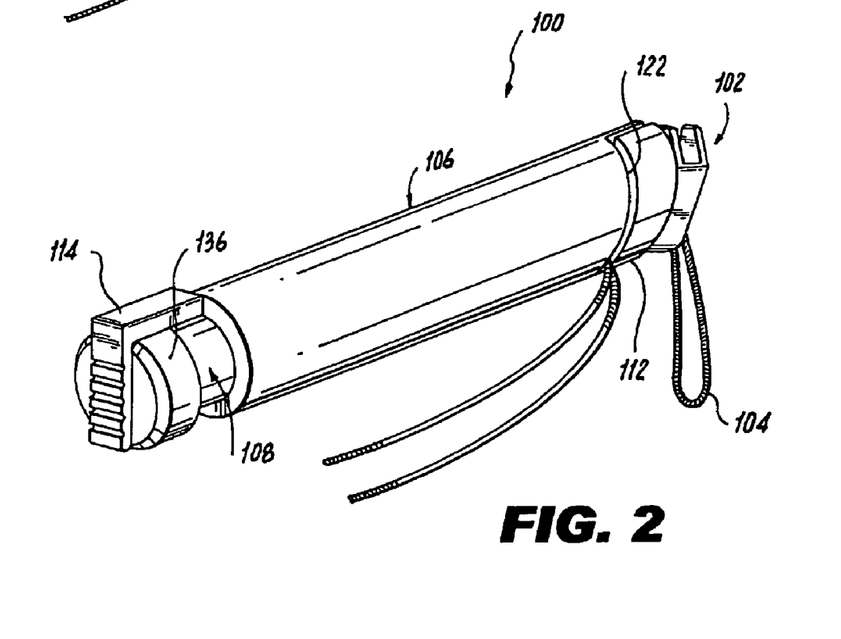
FIG. 2 is a perspective view of the clip applicator of FIG. 1 showing the actuation mechanism associated with the proximal end portion of the clip applicator.

Referring to FIGS. 1 and 2, clip applicator 100 is adapted and configured to apply or otherwise secure a deformable suture clip 102 to a suture at a desired location, to secure the suture in place and ensure effective wound closure. It is envisioned that the clip applicator 100 of the subject invention may be employed in conjunction with a percutaneous procedure, for example, to secure a suture used to close an opening in a blood vessel, or it may be employed in conjunction with a conventional open surgical procedure, for example, to secure a suture used to close an incision or wound in body tissue.

With continuing reference to FIGS. 1 and 2, clip applicator 100 includes an outer tubular body section 106, which has an outer diameter of between about 5 mm to about 10 mm or more, depending upon the application in which the device is employed. The outer body section 106 is adapted and configured to slideably receive and accommodate an inner tubular body section 108 of lesser outer diameter. A mounting fixture or lug 110 mounts on the truncated distal end portion 112 of the outer body section 106 for releasably retaining or otherwise supporting the novel deformable suture clip 102 of the subject invention. In operation, the inner body section 108 is adapted and configured for translation within the outer body section 106 to dislodge the clip 102 from the mounting fixture or lug 110. A safety lockout mechanism 114, which will be discussed in greater detail below, is operatively associated with the proximal end portion of clip applicator 100 to prevent the applicator from being fired until such action is desired. In use, this lockout mechanism prevents the undesired relative movement of the inner and outer body sections, so that the clip cannot be dislodged from the lug.

Figures 3, 4, 5:
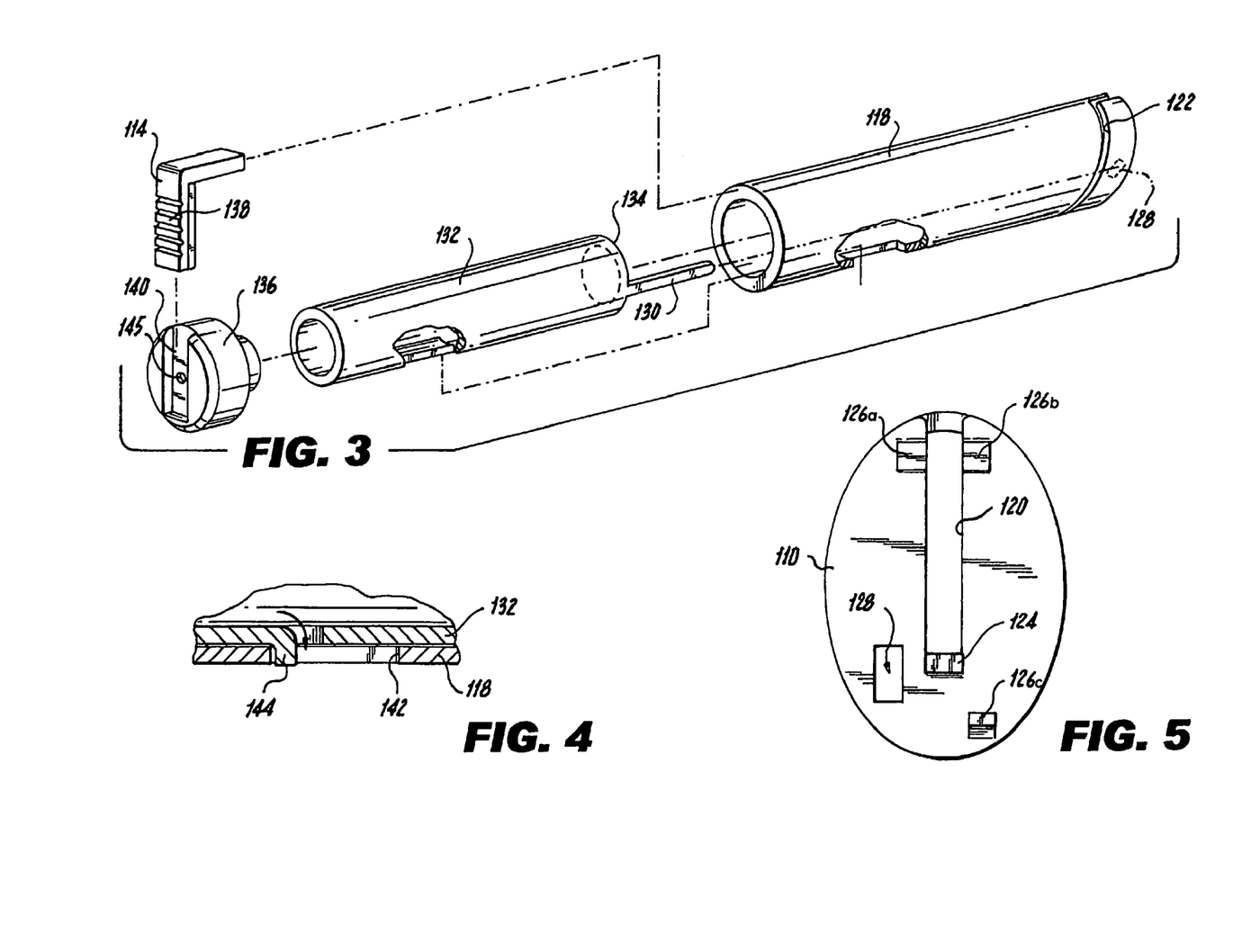
FIG. 3 is an exploded perspective view of the clip applicator of FIG. 1 with parts separated for ease of illustration.
FIG. 4 is a localized cross-sectional view as identified in FIG. 1, illustrating the cooperative engagement between the inner and outer body sections of the clip applicator.
FIG. 5 is a plan view of the lug or mounting fixture disposed on the distal end of the clip applicator, which includes structure for releasably supporting the suture clip.

Referring now to FIG. 3, the outer body section 106 of clip applicator 100 has an elongated tubular housing 118 with a truncated distal end portion 112, as mentioned above. A mounting fixture or lug 110 is disposed at the distal end portion 112 of the housing 118. The lug 110 may be integrally formed or molded with the housing 118, or it may be glued and/or press fit thereto as would be appreciated by those of ordinary skill in the art. Preferably, the lug 110 is angled with respect to the longitudinal axis formed by the housing 118, to ensure proper alignment and placement of the clip relative to a blood vessel during a percutaneous procedure in which the instrument is typically oriented at an angle to the blood vessel.

Referring to FIG. 5, the mounting fixture or lug 110 is generally oval-shaped in order to complimentarily engage the truncated distal end portion 112 of the tubular housing 118. The lug 110 defines a central slot 120 for allowing a surgeon to thread the suture 104 into the housing 118 and out of a passage or slot 122 defined in the side wall of housing 118 (see FIG. 1). The lug 110 has a distally projecting clamp block 124 provided thereon, adjacent to the central slot 120 for retaining or otherwise supporting the suture clip 102 in an open position. The clamp block may be formed integral with the lug or joined thereto in a conventional manner. The lug 110 further includes three integrally formed stop blocks or tabs 126a-126c that engage the clip 102 in predefined locations to align or otherwise maintain the clip 102 in a desired orientation on the lug 110. The lug 110 also defines an opening or aperture 128 for allowing an elongated pusher finger 130 extending distally from the end of the inner body section 108 to access the suture clip 102, and effectuate the dislodgement or ejection of the clip 102 from the lug 110 upon firing the applicator.

Referring again to FIG. 3, the inner body section 108 includes an elongated tubular body 132, which is slideably accommodated within the tubular bore of outer body section 106. The elongated pusher finger 130 extends from a distal end portion of tubular body 132 and is dimensioned and positioned to pass through the opening 128 in lug 110 to eject the suture clip 102 from the distal end of applicator 100. The distal end of tubular body 132 defines a cutting edge or knife blade 134 for severing or cutting the suture 104 disposed in passage 122 of the housing 118, as the clip 102 is dislodged from the lug 110. It is envisioned that the cutting edge or knife blade 134 may be formed integrally with the end of the tubular body 132 or joined thereto in a conventional manner. If the blade 134 is joined to the body 132, it may be formed from a material that is dissimilar to the tubular body 132.

Figures 11, 12:
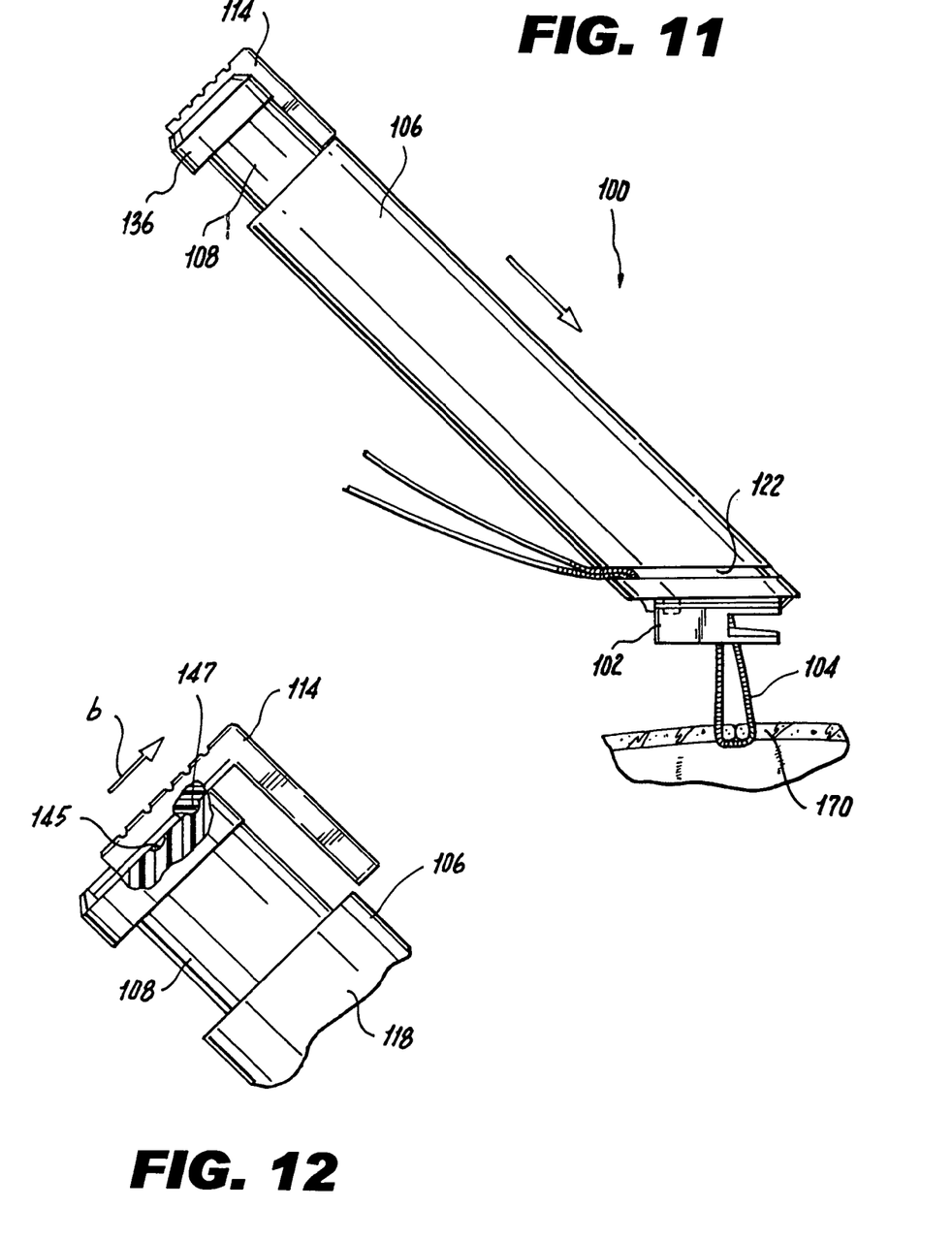
FIG. 11 illustrates the advancement of the clip applicator to the site of an incision in the wall of a blood vessel, with the suture to which the clip is to be applied threaded through the clip and a slot in the distal end of the applicator.
FIG. 12 illustrates the movement of the safety lock-out mechanism from a locked position to an unlocked position so the clip applicator may be fired.

With continuing reference to FIG. 3, an end cap 136 is mounted or otherwise disposed at the proximal end portion of tubular body 132. The end cap 136 has an enlarged outer diameter, relative to the outer body section 106, and thus serves to limit the depth of movement of the tubular body 132 within the housing 118. End cap 136 also supports the safety lockout mechanism 114. The L-shaped lockout mechanism or locking bracket 114 is slideably mounted within a channel 140 formed in end cap 136. The mechanism 114 includes an upper gripping surface 138. A detent or button 147 is formed on the lower surface of the mechanism 114, as best seen in FIG. 12. The detent 147 cooperates with a recess 145 formed within the bottom surface of channel 140 to positively retain the mechanism 114 in a locked position. In a locked or engaged position, the lockout mechanism 114 prevents actuation of the clip applicator 100. This locked position is best seen in FIG. 2. In a disengaged or unlocked position, the lockout mechanism 114 allows actuation of the clip applicator 100, as best seen in FIG. 12.

Referring now to FIG. 4, the housing 118 of outer body section 106 defines an elongated slot or aperture 142 for receiving a locking projection 144 that extends radially outwardly from the tubular body 132 of inner body section 108. The cooperative engagement of these structures serves to prevent axial rotation of the inner body section 108 with respect to the outer body section 106. By maintaining the orientation of the inner and outer body sections, the pusher finger 130 remains aligned with the opening 128 in lug 110. Preferably, locking projection 144 is integrally formed with tubular body 132. Alternatively, the locking projection 144 may be a distinct structure that is selectively mounted to the tubular body 132 after its insertion within the housing 118.

It is envisioned that the components of clip applicator 100 may be formed from a high strength thermoplastic material, such as LEXAN®. In such a case, the clip applicator 100 can be treated as a disposable instrument and discarded after use. Alternatively, the clip applicator 100 of the subject invention may be constructed from stainless steel or a similar surgical grade material that may be sterilized in an autoclave after use.

Figure 6:
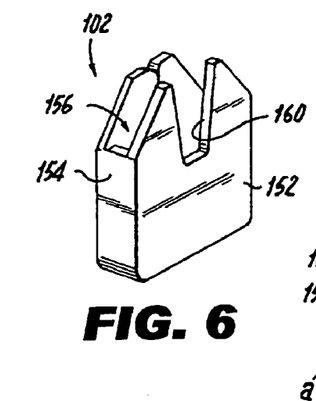
FIG. 6 is a perspective view of a deformable metallic suture clip adapted and configured for use in conjunction with the clip applicator of FIG. 1, wherein the body of the clip is disposed in a normally closed position.
Figure 7:
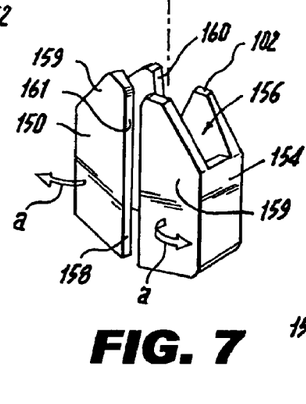
FIG. 7 is a perspective view of the suture clip of FIG. 6, viewed from the proximal surface, wherein the body of the clip is disposed in a deformed or open position.
Figure 8:
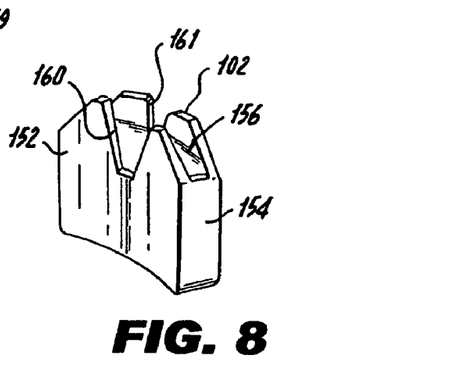
FIG. 8 is a perspective view of the suture clip, viewed from the distal surface, wherein the body of the clip is disposed in an open position.

Turning now to FIGS. 6 through 8, the deformable suture clip 102 of the subject invention is adapted and configured for movement between a normally closed non-deformed position (shown in FIG. 6) and a deformed or flexed open position (shown in FIGS. 7 and 8). In the open or flexed position, a suture 104 can freely pass through the suture clip 102, as shown for example in FIG. 1. However, in the normally closed position, the suture clip 102 securely clamps the suture 104, as shown for example in FIG. 15. Preferably, the suture clip 102 of the subject invention is fabricated from a metallic material, such as a spring metal, a shape memory alloy or the like. It is envisioned however, and well within the scope of the subject disclosure, that the clip may be formed from a resilient plastic material that can be flexed or bent without plastically deforming.

The suture clip 102 is generally rectangular or box-like in configuration and includes opposing proximal and distal surfaces or portions 150 and 152, respectively. Sidewalls 154 extend between the proximal surface 150 and the distal surface 152 to form a channel 156 through the suture clip 102. The proximal surface 150 has a pair of closely spaced panels 159 that form a seam or opening 158 therebetween to accommodate a suture. The seam 158 allows the suture clip 102 to spread open, as denoted by directional arrows "a". In the open position, a suture 104 can pass through the seam 158 and the clip can be mounted on the block 124 of lug 110. Each panel 159 forms an end surface 161 that abuts the corresponding end surface on the opposing panel 159. In the closed position of FIG. 6, the abutting surfaces 161 securely clamp suture 104 therebetween. It is envisioned that the abutting surfaces 161 can be textured or include a coating to enhance the gripping action on the suture.

The distal surface portion 152 of clip 102 forms a notch or groove 160 that substantially aligns with the central slot 120 of the lug 110 when the clip is mounted thereon. The notch 160 allows a surgeon to pass the ends of suture 104 through the notch 160 and central slot 120 when the suture clip 102 is loaded on the clip applicator 100. The distal surface portion 152 of the clip defines the portion of the clip that undergoes the majority of the deformation when the clip is moved to an open position. This portion of the clip may have a reduced thickness relative to the remainder of the clip or it may be formed at least in part from a material that is different from the remainder of the clip.

To load the suture clip 102 on the mounting fixture or lug 110 at the distal end of the clip applicator 100, the suture clip 102 is deformed to open the seam 158. The clamp block 124 is positioned between the seam 158 and the three stops 126 provide banking surfaces to properly position or align the suture clip 102 on the lug 110. At such a time, the abutting surfaces 161 on the panels 159 of the proximal surface portion 150 of the clip 102 are compressed against and otherwise intimately engaged with the clamp block 124. It is envisioned that the suture clip 102 may be loaded onto lug 110 by the surgeon at the time of the procedure, or the clip may be preloaded by the manufacturer.

Figure 9:
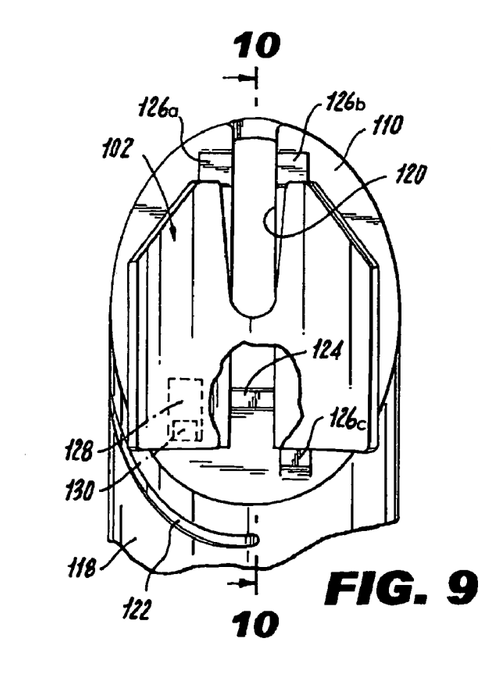
FIG. 9 is a plan view of the distal end of the clip applicator of FIG. 1, with the surgical clip of FIG. 6 supported on the mounting fixture in an open position.
Figure 10:
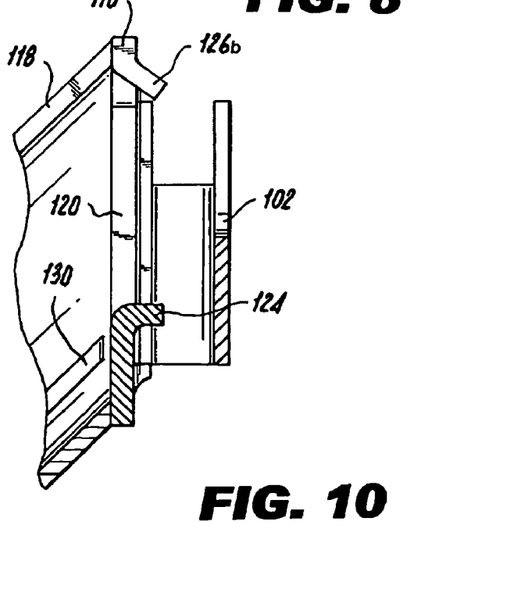
FIG. 10 is a cross-sectional view taken along line 10-10 of FIG. 9, illustrating the manner in which the mounting structures on the lug engage the suture clip.

Referring to FIGS. 9 and 10, the suture clip 102 is shown properly mounted or otherwise releasably maintained on the mounting fixture or lug 110 of clip applicator 100. In this instance, the suture clip 102 is positioned between the three stops 126 to align the seam 158 with the slot 120 in lug 110. The clamp block 124 securely retains the seam 158 in an open position at this time, and the proximal surface portion 150 of the suture clip 102 is located adjacent to the distal surface of lug 110. The notch 160 in the distal surface 152 of the suture clip 102 is also aligned with the central slot 120 of the lug 110 at this time, so that the surgeon can readily thread the ends of the suture 104 through the notch 160, the open seam 158 and central slot 120 of the lug. The ends of the suture 104 pass out of the clip applicator 100 through the passage 122 formed in the side wall of housing 118. When a clip applicator 100 has a suture clip 102 so positioned, the clip applicator 100 is loaded and ready to be fired.

Referring now to FIG. 11, in use the clip applicator 100 is initially advanced to the site of an incision in the wall of a blood vessel 170, with the suture 104 to which the clip 102 is to be applied threaded through the clip 102 and the slot 122 in the distal end of the applicator 100. At such a time, there is slack left in the suture 104. Then the safety lock-out mechanism 114 is moved or slid by the surgeon from the locked position (see FIG. 11) to the un-locked position, in the direction of indicator arrow "b" in FIG. 12.

Figures 13, 14:
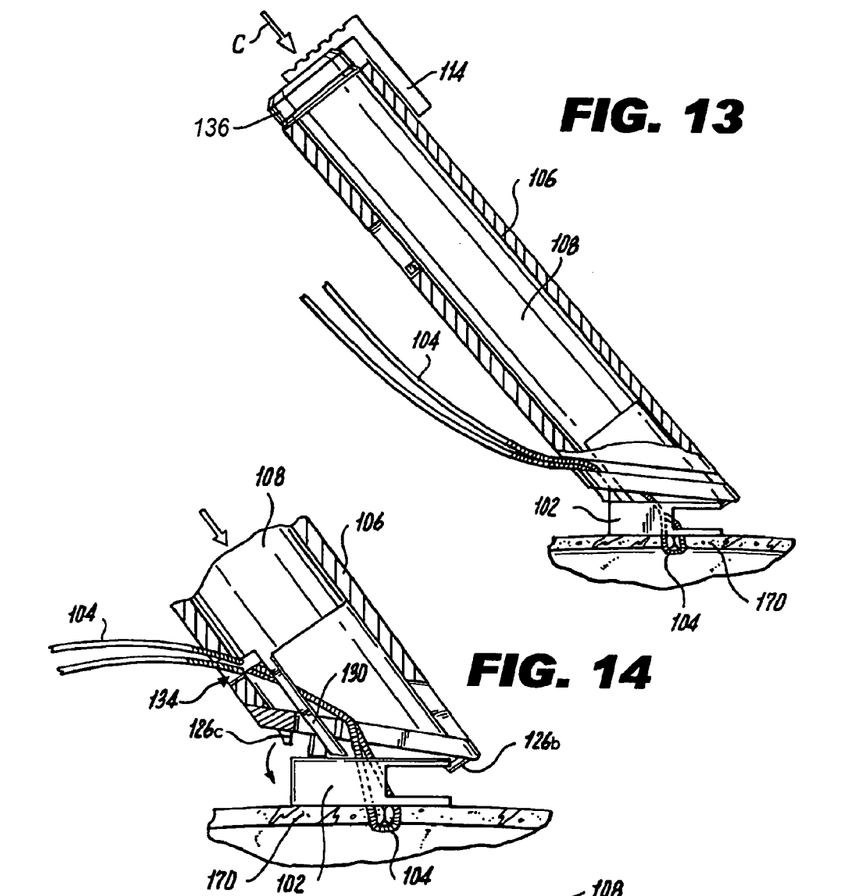
FIG. 13 illustrates the distal advancement of the inner body section relative to the outer body section to effectuate the dislodgment of the clip from the mounting fixture at the distal end of the applicator.
FIG. 14 illustrates the manner in which the pusher finger at the distal end of the inner body section dislodges or ejects the clip from the mounting fixture at the distal end of the outer body section, as the cutting blade simultaneously severs the suture.
Figure 15:
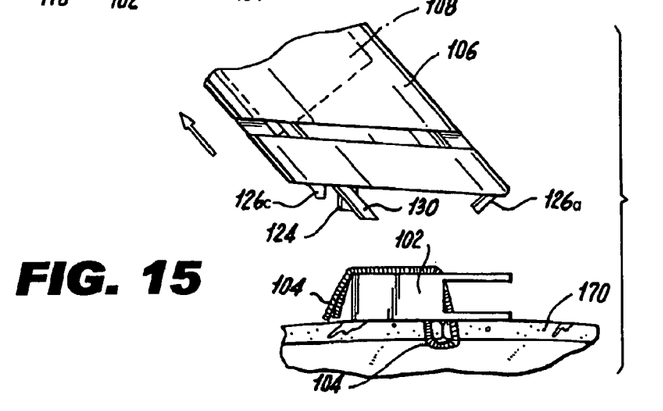
FIG. 15 illustrates the withdrawal of the clip applicator from the site of the incision after the clip has been dislodged from the mounting fixture and the suture has been cut at a location proximal to the clip.

Thereafter, the suture 104 is pulled tight by the surgeon from a remote location to take up any slack. At such a time, the applicator 100 is fired. This is done by effectuating the distal advancement of the inner body section 108 into the outer body section 106 in the direction of indicator arrow "c" in FIG. 13. Upon firing, the pusher finger 130 at the distal end of the inner body section 108 dislodges or ejects the clip 102 from the mounting fixture 110 at the distal end of the outer body section 106. Shortly thereafter, the cutting blade 134 severs the suture 104 proximal to the suture clip 102. Then, as shown in FIG. 15, the clip applicator 100 is withdrawn from the site of the incision in blood vessel 170.

After a period time in which the suture 104 and suture clip 102 have performed their usefulness, e.g., hemostasis occurs, the suture clip 102 and suture 104 may be removed by deforming the suture clip 102 to the open position. After removing the suture clip 102, the suture 104 may be removed from the suture location on blood vessel 170 or, if dissolvable, left in place.

While the subject invention has been described with respect to preferred embodiments, those skilled in the art will readily appreciate that various changes and/or modifications can be made to the invention without departing from the spirit or scope of the invention as defined by the appended claims.

What is claimed is:

1. A system for securing a suture at an incision site comprising:
   a) a deformable suture clip having opposed spaced apart distal and proximal ends, the proximal end including a pair of closely spaced panels that define a proximal surface of the clip, the distal end including a deformable distal end surface and connecting the closely spaced panels, such that the clip is configured for movement between a deformed flexed open position wherein a suture can pass between the two panels and a non-deformed closed position wherein the suture can be securely clamped between the two panels, wherein the suture clip is configured to be normally in the non-deformed closed position; and
   b) a clip applicator including an elongated body defining a longitudinal axis and having opposed proximal and distal ends, the distal end of the body defining a distal end face with a mounting fixture having means for supporting the clip such that the proximal surface of the pair of closely spaced panels of the clip abuts the distal end face of the applicator with the two closely spaced panels defining the proximal surface of the clip spread into the deformed flexed open position, the clip applicator including means for dislodging the suture clip from the mounting fixture, the dislodging means being adapted for movement between an initial fully retracted position wherein the clip is supported by the mounting fixture in the deformed flexed open position and a second extended position wherein the clip is disengaged from the mounting fixture such that the two panels of the clip move to the non-deformed closed position to securely clamp the suture therebetween.

2. A system as recited in claim 1, wherein the clip applicator further includes means for severing the suture and the severing means operates simultaneously with the dislodging of the suture clip from the mounting fixture.

3. A system as recited in claim 1, wherein the distal end of the body is truncated such that the distal end face is oriented at an angle to the longitudinal axis of the clip applicator.

4. A system as recited in claim 1, wherein the means for supporting the suture clip in an open position includes a clamp block, extending distally from the mounting fixture, for insertion between the closely spaced panels of the suture clip.

5. A system as recited in claim 1, wherein the means for dislodging the suture clip from the mounting fixture includes a slideable pusher finger adapted to urge the clip in a distal direction, wherein the mounting fixture includes an opening dimensioned and configured to provide the pusher finger with access to the suture clip.

6. A system as recited in claim 5, wherein the means for dislodging the clip is operable from the proximal end of the clip applicator.

7. A system as recited in claim 1, wherein the closely spaced panels of the suture clip include abutting surfaces to securely clamp the suture therebetween.

8. A system as recited in claim 1, wherein the means for supporting the suture clip in an open position includes a projection for maintaining the clip in the open position, wherein the projection is squeezed between the closely spaced panels of the suture clip and thereby the projection assists the mounting feature in holding the suture clip.

9. A system for securing a suture at an incision site comprising:
   a) a clip applicator having an elongate body that defines a longitudinal axis and includes opposed proximal and distal ends, wherein the distal end of the body includes a planar clip mounting face with a lug;
   b) a clamp block extending distally outward from the planar mounting face at the distal end of the body of the clip applicator;
   c) a clip including a pair of closely spaced panels configured for movement between a deformed flexed open position wherein a suture can pass between the two panels and a non-deformed closed position wherein the suture can be securely clamped between the two panels, the pair of closely spaced panels clamping the clamp block therebetween in the open position in which the panels abut the mounting face of the body of the clip applicator; and
   d) a pusher finger operably connected to the clip applicator and mounted to extend though an opening defined in the clip mounting face of the body of the clip applicator for dislodging the clip from the clamp block of the applicator, whereby upon dislodgment of the clip from the applicator a suture extending between the pair of closely spaced panels will be secured by the clip in the closed position.

10. A system for securing a suture at an incision site as recited in claim 9, further comprising safety means on the clip applicator to prevent premature disengagement of the clip.

11. A system for securing a suture at an incision site as recited in claim 9, wherein the pusher finger is operable from the proximal end of the clip applicator.

12. A system for securing a suture at an incision site as recited in claim 9, wherein the clip applicator includes an outer shell assembly having a housing defining an aperture and a passage and an inner shell assembly at least partially engaged within the outer shell assembly, the inner shell assembly having a tubular body extending into the passage, wherein the tubular body is operatively connected to the pusher finger.

13. A system for securing a suture at an incision site as recited in claim 12, further comprising a safety slidably mounted on the inner shell assembly for limiting insertion of the tubular body into the passage.

14. A system for securing a suture at an incision site as recited in claim 9, wherein the clip applicator further includes means for severing the suture configured and adapted to operate simultaneously with the dislodging of the suture clip from the mounting fixture.

15. A system for securing a suture at an incision site as recited in claim 9, wherein the distal end of the body of the clip applicator is truncated such that the clip mounting face of the body of the clip applicator is oriented at an angle with respect to the longitudinal axis of the clip applicator.

16. A system for securing a suture at an incision site as recited in claim 9, wherein the closely spaced panels of the clip include abutting surfaces configured and adapted to securely clamp the suture therebetween.

17. A system for securing a suture at an incision site as recited in claim 9, wherein the clip substantially covers the distal end of the clip applicator.

18. A system for securing a suture at an incision site as recited in claim 9, wherein the clip has a sidewall extending from each of the closely spaced panels to a distal surface portion of the clip so as to form a channel between the sidewalls, closely spaced panels, and distal surface portion of the clip.

19. A system for securing a suture at an incision site as recited in claim 18, wherein the distal surface portion of the clip is relatively thinner than the two sidewalls and the two closely spaced panels.

20. A system for securing a suture at an incision site as recited in claim 18, wherein, the clip is configured and adapted so that when it is dislodged from the applicator, the distal surface portion of the clip is substantially parallel to two closely spaced panels of the clip and substantially perpendicular the two sidewalls.

21. A system for securing a suture at an incision site as recited in claim 18, wherein the distal surface portion of the clip includes a notch aligned with an opening between the closely spaced panels of the clip, wherein the clip mounting face of the distal end of the body of the clip applicator defines a slot aligned with the opening between the closely spaced panels of the clip, and wherein the notch of the clip and the slot of the clip applicator are configured to receive a suture therethrough when a suture is placed between the closely spaced panels of the clip.

* * * * *